(12) United States Patent
Sniffin et al.

(10) Patent No.: US 10,709,442 B2
(45) Date of Patent: Jul. 14, 2020

(54) STITCHING DEVICE WITH LONG NEEDLE

(71) Applicant: Covidien LP, Mansfield, MA (US)

(72) Inventors: Kevin Sniffin, Danbury, CT (US);
Mark Russo, Plantsville, CT (US);
Gregory Fischvogt, Hamden, CT (US);
Russell Pribanic, Roxbury, CT (US);
Eric Taylor, East Hampton, CT (US)

(73) Assignee: COVIDIEN LP, Mansfield, MA (US)

( * ) Notice: Subject to any disclaimer, the term of this patent is extended or adjusted under 35 U.S.C. 154(b) by 442 days.

(21) Appl. No.: 15/587,691

(22) Filed: May 5, 2017

(65) Prior Publication Data

US 2017/0231624 A1    Aug. 17, 2017

Related U.S. Application Data

(63) Continuation of application No. 14/465,865, filed on Aug. 22, 2014, now Pat. No. 9,675,340.

(60) Provisional application No. 61/906,554, filed on Nov. 20, 2013.

(51) Int. Cl.
*A61B 17/04*    (2006.01)
*A61B 17/06*    (2006.01)
*A61B 17/062*   (2006.01)

(52) U.S. Cl.
CPC .... *A61B 17/06066* (2013.01); *A61B 17/0469* (2013.01); *A61B 17/0625* (2013.01); *A61B 2017/0609* (2013.01); *A61B 2017/06095* (2013.01)

(58) Field of Classification Search
CPC .............. A61B 2017/06071; A61B 2017/0609
See application file for complete search history.

(56) References Cited

U.S. PATENT DOCUMENTS

| | | | |
|---|---|---|---|
| 1,037,864 A | 9/1912 | Carlson et al. | |
| 1,131,163 A | 3/1915 | Saunders et al. | |
| 1,293,565 A | 2/1919 | Smit | |
| 1,449,087 A | 3/1923 | Bugbee | |
| 1,876,792 A | 9/1932 | Thompson | |
| 2,213,830 A | 9/1940 | Anastasi | |
| 2,880,728 A | 4/1959 | Rights | |
| 3,090,386 A | 5/1963 | Curtis | |
| 3,349,772 A | 10/1967 | Rygg | |
| 3,470,875 A | 10/1969 | Johnson | |
| 3,807,407 A | 4/1974 | Schweizer | |
| 3,842,840 A | 10/1974 | Schweizer | |
| 3,901,244 A | 8/1975 | Schweizer | |
| 3,946,740 A | 3/1976 | Bassett | |
| 4,021,896 A | 5/1977 | Stierlein | |
| 4,109,658 A | 8/1978 | Hughes | |
| 4,161,951 A | 7/1979 | Scanlan, Jr. | |
| 4,164,225 A | 8/1979 | Johnson et al. | |
| 4,236,470 A * | 12/1980 | Stenson | A61B 16/00 112/169 |
| 4,345,601 A | 8/1982 | Fukuda | |
| 4,373,530 A | 2/1983 | Kilejian | |

(Continued)

*Primary Examiner* — Julie A Szpira
(74) *Attorney, Agent, or Firm* — Carter, DeLuca & Farrell LLP

(57) ABSTRACT

A needle for use with an endoscopic stitching device includes a first end portion that is movable relative to a second end portion to allow the needle to convert from a first, mis-aligned orientation to a second, aligned orientation, thereby allowing the length of the needle in the aligned orientation to exceed the height of an end effector.

13 Claims, 5 Drawing Sheets

(56) References Cited

U.S. PATENT DOCUMENTS

| | | | | |
|---|---|---|---|---|
| 4,471,781 A | | 9/1984 | Di Giovanni et al. | |
| 4,491,135 A | | 1/1985 | Klein | |
| 4,580,567 A | | 4/1986 | Schweitzer et al. | |
| 4,621,640 A | | 11/1986 | Mulhollan et al. | |
| 4,635,638 A | | 1/1987 | Weintraub et al. | |
| 4,890,615 A | | 1/1990 | Caspari et al. | |
| 4,923,461 A | | 5/1990 | Caspari et al. | |
| 4,935,027 A | | 6/1990 | Yoon | |
| 4,957,498 A | | 9/1990 | Caspari et al. | |
| 5,059,201 A | | 10/1991 | Asnis | |
| 5,100,421 A | | 3/1992 | Christoudias | |
| 5,171,257 A | | 12/1992 | Ferzli | |
| 5,181,919 A | * | 1/1993 | Bergman | A61B 17/0469 606/139 |
| 5,207,693 A | | 5/1993 | Phillips | |
| 5,217,471 A | | 6/1993 | Burkhart | |
| 5,242,458 A | | 9/1993 | Bendel et al. | |
| 5,254,126 A | | 10/1993 | Filipi et al. | |
| 5,261,917 A | | 11/1993 | Hasson et al. | |
| 5,281,220 A | | 1/1994 | Blake, III | |
| 5,336,230 A | | 8/1994 | Leichtling et al. | |
| 5,454,823 A | * | 10/1995 | Richardson | A61B 17/0469 606/145 |
| 5,569,301 A | * | 10/1996 | Granger | A61B 17/0469 606/223 |
| 5,591,181 A | * | 1/1997 | Stone | A61B 17/0469 206/239 |
| 5,674,229 A | | 10/1997 | Tovey et al. | |
| 5,690,652 A | * | 11/1997 | Wurster | A61B 17/0469 606/139 |
| 5,693,071 A | * | 12/1997 | Gorecki | A61B 17/0469 606/222 |
| 5,814,054 A | * | 9/1998 | Kortenbach | A61B 17/0469 606/139 |
| 5,980,538 A | * | 11/1999 | Fuchs | A61B 17/0469 606/139 |
| 6,056,771 A | * | 5/2000 | Proto | A61B 17/0469 606/222 |
| 6,126,666 A | * | 10/2000 | Trapp | A61B 17/0469 206/339 |
| 6,224,614 B1 | * | 5/2001 | Yoon | A61B 17/062 606/147 |
| 6,270,508 B1 | * | 8/2001 | Klieman | A61B 17/062 606/147 |
| 8,337,515 B2 | | 12/2012 | Viola et al. | |
| 8,454,631 B2 | * | 6/2013 | Viola | A61B 17/0469 606/144 |
| 8,628,545 B2 | * | 1/2014 | Cabrera | A61B 17/0469 606/144 |
| 8,876,701 B2 | * | 11/2014 | Surti | A61B 1/00087 600/104 |
| 8,968,339 B2 | * | 3/2015 | Malkowski | A61B 17/0625 606/144 |
| 9,072,480 B2 | * | 7/2015 | Hart | A61B 1/00066 |
| 9,271,720 B2 | * | 3/2016 | Stone | A61B 17/0482 |
| 9,675,340 B2 | | 6/2017 | Sniffin et al. | |
| 9,913,639 B2 | * | 3/2018 | Woodard, Jr. | A61B 17/0469 |
| 2004/0260314 A1 | * | 12/2004 | Lizardi | A61B 17/0469 606/144 |
| 2005/0149066 A1 | * | 7/2005 | Stafford | A61B 17/0057 606/144 |
| 2006/0020274 A1 | * | 1/2006 | Ewers | A61B 17/0469 606/148 |
| 2009/0221868 A1 | * | 9/2009 | Evans | A61B 17/0401 600/37 |
| 2009/0299406 A1 | * | 12/2009 | Swain | A61B 17/0469 606/215 |
| 2010/0228270 A1 | * | 9/2010 | Bogart | A61B 17/0469 606/144 |
| 2011/0112555 A1 | * | 5/2011 | Overes | A61B 17/0491 606/145 |
| 2011/0257663 A1 | * | 10/2011 | Unsworth | A01K 91/04 606/144 |
| 2012/0123471 A1 | * | 5/2012 | Woodard, Jr. | A61B 17/06004 606/223 |
| 2013/0023725 A1 | * | 1/2013 | Nose | A61B 17/06109 600/30 |

\* cited by examiner

STITCHING DEVICE WITH LONG NEEDLE

CROSS-REFERENCE TO RELATED APPLICATIONS

This application is a continuation of U.S. patent application Ser. No. 14/465,865, filed Aug. 22, 2014, which claims benefit of and priority to U.S. Provisional Application No. 61/906,554, filed Nov. 20, 2013, and the disclosures of each of the above-identified applications are hereby incorporated by reference in their entirety.

TECHNICAL FIELD

The present disclosure relates to devices, systems, and methods for endoscopic suturing or stitching and, more particularly, to end effectors, systems and methods for endoscopic suturing and/or stitching through an access device such as a cannula.

BACKGROUND

Increasingly, more and more surgical procedures are being performed through small openings (e.g., an incision or a natural opening) in the skin with the goal of reducing the invasiveness of the procedures. As compared to the larger openings typically required in traditional procedures, smaller openings result in less trauma to the patient. By reducing the trauma to the patient, the time required for recovery is also reduced. Generally, the surgical procedures that are performed through small openings in the skin are referred to as "endoscopic." If the procedure is performed on the patient's abdomen, the procedure is referred to as "laparoscopic." Throughout the present disclosure, the term "minimally invasive" is to be understood as encompassing both endoscopic and laparoscopic procedures. Cannulas can be utilized during a minimally invasive procedure to facilitate passage of endoscopic instruments.

In many surgical procedures, including those involved in endoscopic surgery, it is often necessary to suture bodily organs or tissue. Endoscopic suturing procedures can be challenging due to the small openings through which the suturing of bodily organs or tissues must be accomplished. Typically, the dimensions of the needles of endoscopic stitching devices are restricted by spatial limitations of the cannulas utilized to introduce the stitching devices into the surgical site.

It would be advantageous to have an end effector of an endoscopic stitching device that can be advanced through spatially limited access devices (e.g., cannulas) while supporting long needles. The advancement of stitching devices with long needles into surgical sites would enable a clinician to suture tissue with larger thickness as compared to stitching devices with short needles.

SUMMARY

Various embodiments of endoscopic stitching needles for use with an endoscopic stitching device are described, wherein the needle includes a first end portion that is movable relative to a second end portion. Being movable, the first end portion of the needle can be in a first, misaligned orientation relative to the second end portion of the needle. The first end portion of the needle can then be moved into a second, aligned orientation relative to the second end portion of the needle. The first end portion of the needle is adapted to engage a first jaw member of the endoscopic stitching device and the second end portion is adapted to engage a second jaw member of the endoscopic stitching device.

In embodiments of the needle, the first end portion pivots relative to the second end portion.

In some embodiments of the needle, a connecting portion is disposed between the first and second end portions. The connecting portion may be formed of a flexible material adapted to enable the first end portion to pivot relative to the second end portion.

In embodiments of the needle, the first end portion includes a locking feature and the second end portion includes a mating feature.

In certain embodiments of the needle, the connecting portion includes a first arm member that extends from the first end portion and a second arm member that extends from the second end portion. The first arm member may be secured to the second arm member by a pivot pin.

In embodiments of the needle, the first arm member includes the locking feature and the second arm member includes the mating feature. The locking feature and the mating feature are configured to selectively engage each other to at least temporarily lock the first and second end portions of the needle in an aligned configuration.

In certain embodiments of the needle, the first and second end portions are separate, and the first end portion of the needle is adapted to connect to the second end portion of the needle. The locking feature and the mating feature can be adapted to connect to form the first and second end portions into a unitary arrangement. The first and second end portions can be movable relative to each other between a first, misaligned position and a second, aligned position. In embodiments, the first and second end portions are adapted to connect in the second, aligned position.

In embodiments of the needle, the first end portion is adapted to receive the second end portion. The first end portion and the second end portion can support a compressible element adapted to enable the first and second end portions to move between a first, compressed position and a second, extended position. The compressible element can include at least one of a spring and a gas.

According to one aspect, an endoscopic stitching device includes an end effector and a needle.

The end effector of the endoscopic stitching device includes a first jaw member and a second jaw member. The first jaw member is movable relative to the second jaw member between an open state and a closed state. The end effector defines a height in the closed state that is measured between a bottom-most surface of the end effector and a top-most surface of the end effector.

In some embodiments, the needle defines a working length that is greater than the height of the end effector.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Minimally invasive suturing devices in accordance with the present disclosure enable the use of a needle that is longer than a width of a suturing device and/or an access device used to deliver the suturing device to the surgical site. Delivery of such a relatively long needle is achieved by moving a first portion of the needle relative to a second portion of the needle in a first direction to reduce a profile of the needle from a suturing state to an insertion state. In the insertion state of the needle, the needle can be retained by an end effector of the suturing device while the end effector is disposed in a first, insertion position. Once delivered to the surgical site, the needle can be reoriented to the suturing state, e.g., by moving the first portion of the needle in a second direction relative to the second portion of the needle where the second direction is opposite the first direction. When in the suturing state, minimally invasive suturing can be achieved by passing the needle back and forth between opposed jaw members of the end effector in a conventional manner.

For a more detailed description of suitable endoscopic surgical devices, systems, and methods for use with the various end effectors and needles described herein, reference can be made, for example, to U.S. Pat. No. 8,337,515 and to U.S. Patent Application Publication No. 2009/0312773, the entire contents of each of which are incorporated herein by reference. Details of various embodiments of minimally invasive suturing devices in accordance with the present disclosure will now be described in detail.

As used in the following detailed description, the term "clinician" refers to a doctor, nurse, or other health care provider and may include support personnel. The terms "proximal" or "trailing" each refer to a portion of a structure closer to a clinician, and the terms "distal" or "leading" each refer to a portion of a structure farther from the clinician.

Figure 1:
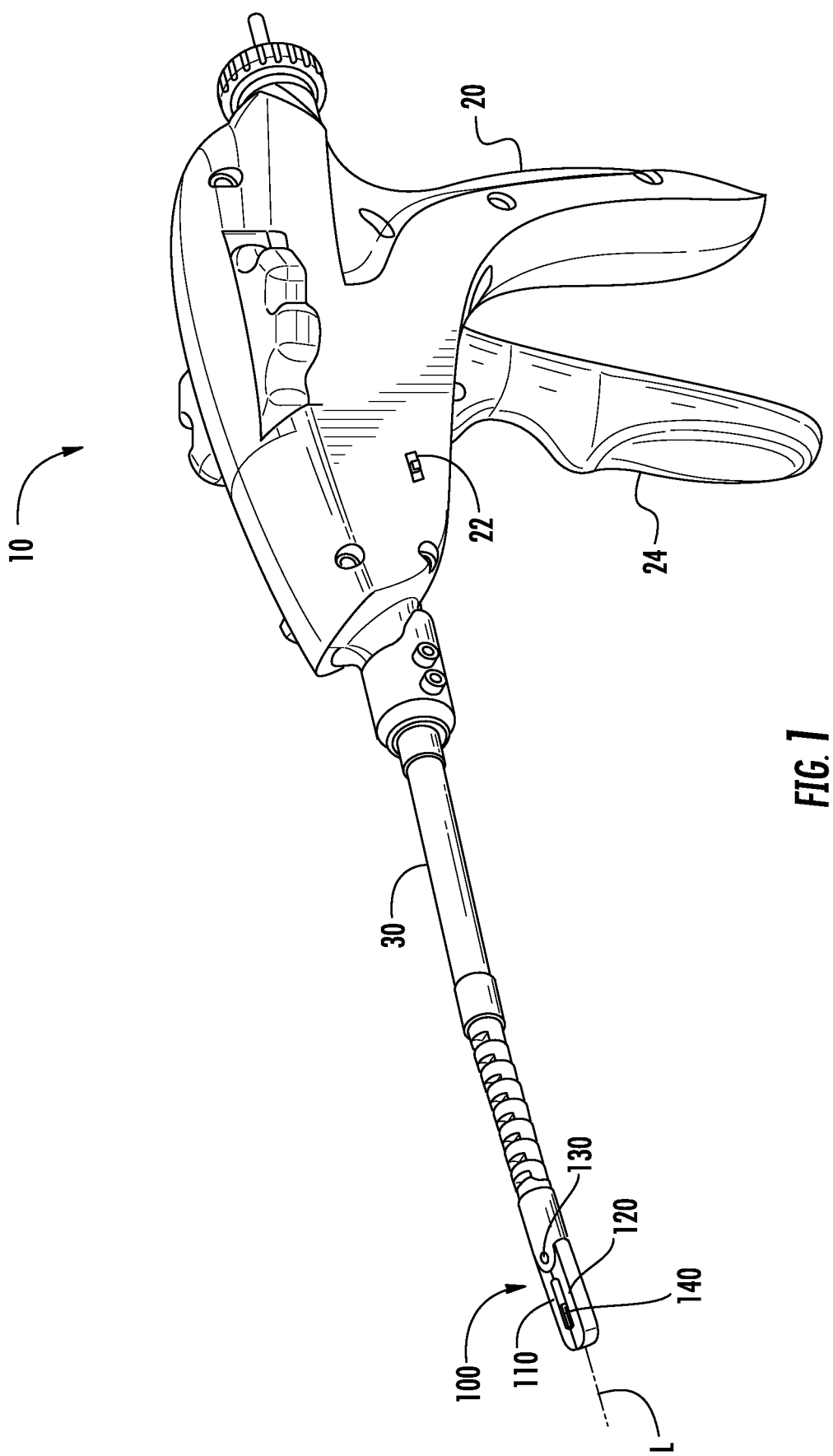
FIG. 1 is a perspective view of an embodiment of an endoscopic stitching device in accordance with the present disclosure.

Referring now in specific detail to the drawings, in which like reference numbers identify similar or identical elements, FIG. 1 illustrates an endoscopic stitching device, shown generally at 10. Endoscopic stitching device 10 includes a handle assembly 20 with an actuator 22, a trigger 24, and/or other suitable actuating mechanism (e.g., a robot, etc.). As can be appreciated, actuator 22 can be any suitable slide, knob, button, or the like. An elongate tubular body portion 30 extends distally from handle assembly 20 and defines a longitudinal axis "L" that extends through proximal and distal end portions of elongate tubular body portion 30. An end effector 100 is supported on the distal end portion of elongate tubular body portion 30 and can be remotely operable by handle assembly 20. End effector 100 is adapted to be particularly useful in endoscopic or laparoscopic procedures wherein an endoscopic portion of the stitching device, i.e., end effector 100, is insertable into a surgical site, via an access device (e.g., cannula) (not shown) or the like.

Figure 2A:
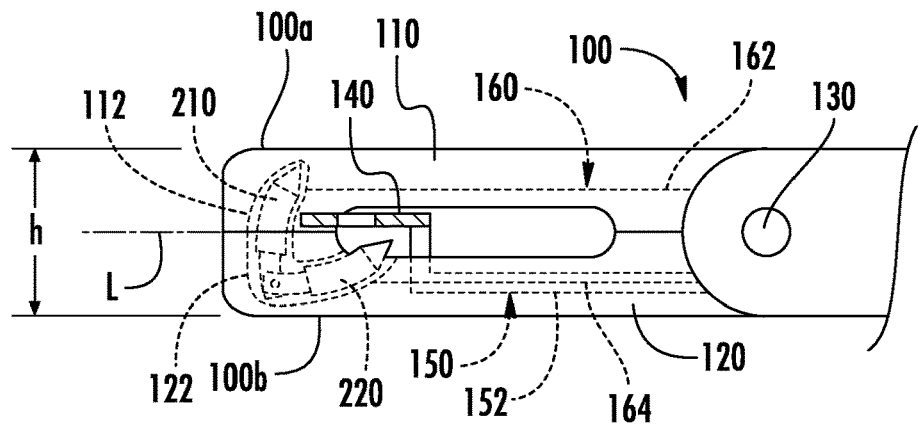
FIG. 2A is a side view of a distal end portion of an embodiment of an end effector of the endoscopic stitching device of FIG. 1, the end effector shown in an insertion state and supporting an embodiment of a needle of the present disclosure, the needle being shown in an unlocked state.
Figure 2B:
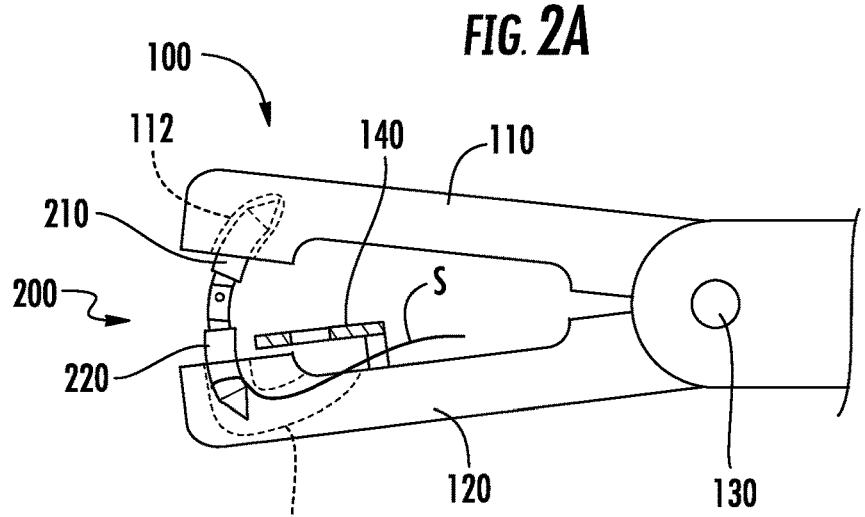
FIG. 2B is a side view of the distal end portion of the end effector of FIG. 2A shown in a stitching state and supporting the needle of FIG. 2A in a locked state.
Figure 2C:
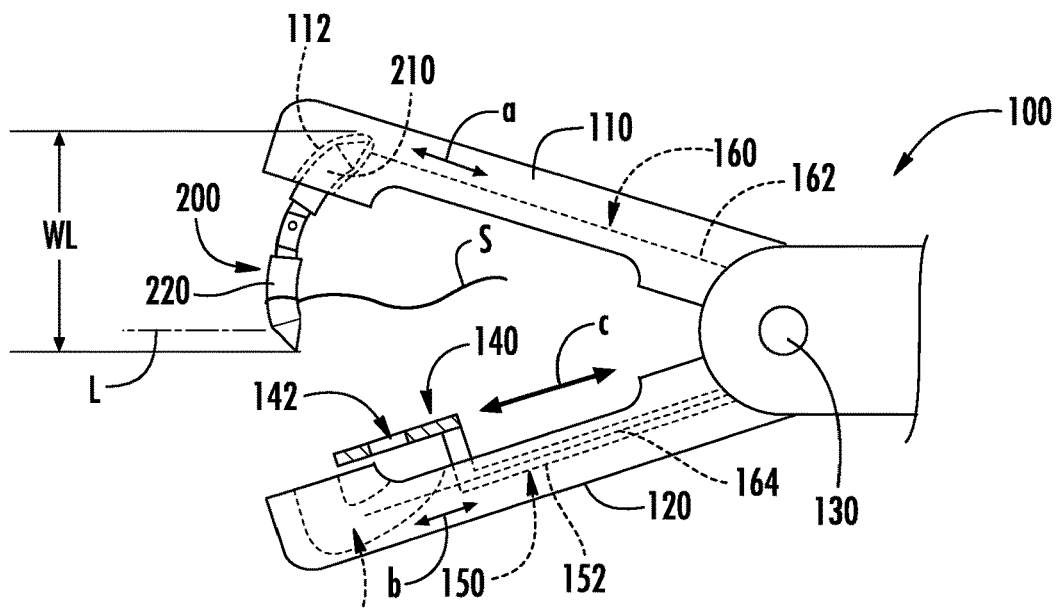
FIG. 2C is a side view of the distal end portion of the end effector of FIGS. 2A and 2B shown in an open state and supporting the needle of FIG. 2A in the locked state.

FIGS. 2A-2C illustrate the details of end effector 100. End effector 100 has a top-most surface 110a and a bottom-most surface 110b and is adapted to move between a closed state (FIG. 2A), a stitching state (FIG. 2B), and an open state (FIG. 2C). In the closed state, end effector 100 defines a height "h" that is measured between top-most surface 110a and bottom-most surface 110b. End effector 100 includes a first jaw member 110 and a second jaw member 120 that are pivotably coupled by a pin 130. Each jaw member 110, 120 releasably supports a surgical needle such as a surgical needle 200, described in greater detail below. As seen in FIGS. 2B and 2C, a suture "S" can be secured to the needle, using any conventional method, before insertion of end effector 100 into the surgical site or shortly after insertion of end effector 100 into the surgical site. For example, the suture "S" can be secured to any of the presently described needles by tying and/or knotting the suture "S" to a respective one of the needles (e.g., by looping around an outer surface of the respective needle). Alternatively, and or additionally, any of the presently described needles can define any number of apertures (not shown) into and/or through which suture "S" may be secured.

First jaw member 110 defines a first needle receiving recess 112 and second jaw member 120 defines a second needle receiving recess 122. Each needle receiving recess 112, 122 is adapted to receive an end portion of a needle (e.g., needle 200) in releasable friction fit relation. As illustrated in FIGS. 2A and 2B, upon opening of end effector 100 from the closed state to the stitching state, second needle receiving recess 122 is dimensioned to cam the surgical needle from an insertion position or unlocked state, where the surgical needle can be compressed or bent, to a stitching position or locked state, where the surgical needle is extended or elongated and at least temporarily locked.

As described in U.S. Pat. No. 8,337,515 referenced above and as shown in FIGS. 2A and 2C, each of first and second jaw members 110, 120 can support a grasping member 160 such as grasping members 162, 164. Grasping members 162, 164 are axially movable, as indicated by arrows "a" and "b," to enable a needle to be passed back and forth between the first and second jaw members 110, 120. More particularly, to enable a needle to be passed back and forth between first and second jaw members 110, 120, each grasping member 162, 164 can releasably engage an opposite end portion of a needle, alternately with the other grasping member 162, 164. As can be appreciated, any of the presently described needles can define a single opening that extends between opposite end portions of the needle, and, in some embodiments, the presently described needles can define one or more openings on opposed ends of the respective needles such that grasping members 162, 164 can secure a needle to one of jaw members 110, 120 when a respective one of grasping members 162, 164 is engaged with a respective one of the opening(s).

As seen in FIG. 2C, end effector 100 includes a guide member 140 that defines an opening 142. With continued reference to FIGS. 2A-2C, guide member 140 is operatively coupled to second jaw member 120 and is selectively axially movable along second jaw member 120, as indicated by arrow "c," between proximal and distal positions, including various intermediate positions. Guide member 140 can be operatively coupled to an actuation mechanism 150. Actuation mechanism 150 includes a shaft member 152 (e.g., a cable) having a distal end portion that is coupled to the guide member 140 and a proximal end portion that is coupled to actuator 22 (FIG. 1) of the handle assembly 20 such that an actuation of actuator 22 translates shaft member 152 to cause guide member 140 to translate between the proximal and distal positions.

In embodiments, actuation mechanism 150 can include any suitable mechanical and/or electrical component adapted to impart axial translation to guide member 140. For example, actuation mechanism 150 can include any number of springs, levers, gears, cables, electrical circuitry, and the like that are adapted to cooperate to translate guide member 140 between the proximal and distal positions.

Figure 3A:
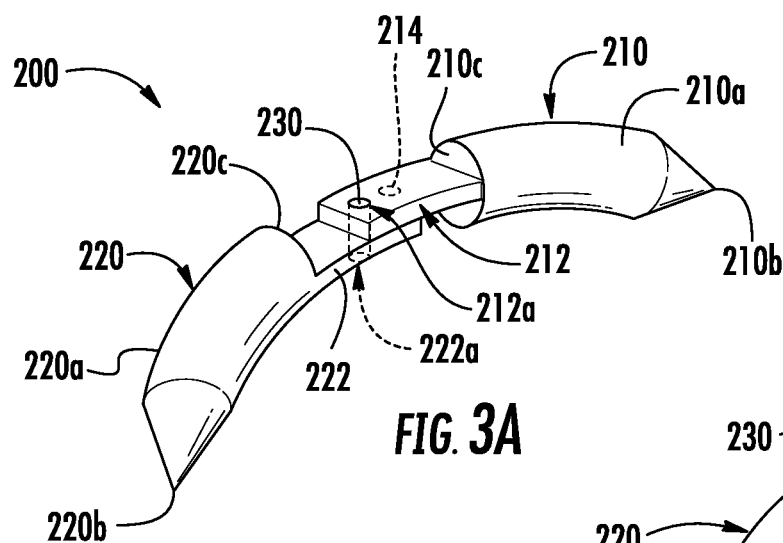
FIG. 3A is an enlarged, perspective view illustrating the needle of FIGS. 2A and 2B in a locked state.
Figure 3B:
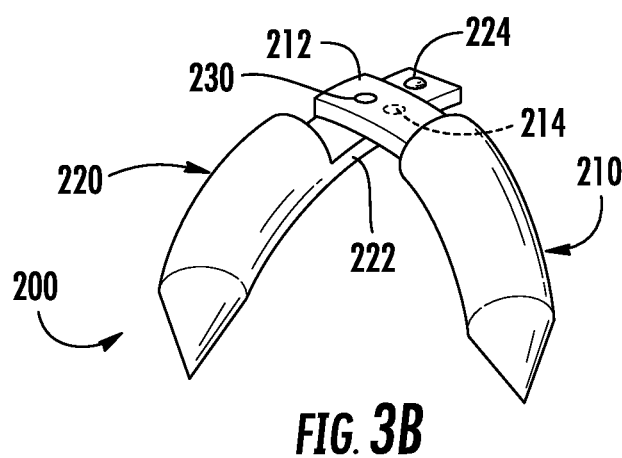
FIG. 3B is a perspective view of the needle of FIG. 3A shown in an unlocked state.

FIGS. 3A and 3B illustrate an embodiment of a needle, shown generally as 200, for use with an end effector of an endoscopic stitching device such as end effector 100. As depicted in FIG. 2C, each of the presently described needles, including needle 200, defines a working length "WL" and each is adapted to support a suture "S" for effectuating a suturing procedure, which, as described above, can be secured to any of the presently described needles in any conventional manner.

The working length "WL" of the any of the presently described needles can be any suitable dimension. In some embodiments, the working length "WL" is greater than height "h" (see FIGS. 2A and 2C) of any of the presently described end effectors in the closed state. In other embodiments, the working length "WL" is less than or equal to height "h" of any of the presently described end effectors in the closed state.

With reference to FIG. 3A, needle 200 includes a first end portion 210 and a second end portion 220 that are operatively coupled together. First end portion 210 includes a first body 210a having a first tip end 210b and a first support end 210c. First end portion 210 includes a first arm 212 that extends from first support end 210c so as to be cantilevered from first end portion 210. First arm 212 may be integrally formed with, or separately connectable to, first support end 210c of first body 210a. Although shown extending from a central portion of first support end 210c, first arm 212 can extend from any suitable portion of first support end 210c. First arm 212 defines a first pin receiving passage 212a and includes a mating or locking feature 214 (e.g., a recess, adhesive, protuberance, or the like).

With continued reference to FIG. 3A, second end portion 220 includes a second body 220a having a second tip end 220b and a second support end 220c. Second end portion 220 includes a second arm 222 that extends from second support end 220c so as to be cantilevered from second end portion 220. Second arm 222 may be integrally formed with, or separately connectable to, second support end 220c. Although shown extending from a bottom portion of second support end 220c, second arm 222 can extend from any suitable portion of second support end 220c. Second arm 222 includes a mating or locking feature 224 (e.g., a recess, adhesive, protuberance, or the like) and defines a second pin receiving passage 222a that is identical to first pin receiving passage 212a. As can be appreciated, mating or locking feature 224 of second end portion 220 is complementary to mating or locking feature 214.

As seen in FIGS. 3A and 3B, first and second arms 212, 222 of needle 200 are positioned in an offset and/or overlapping arrangement and secured together by a pin 230 that extends through first and second pin receiving passages 212a, 222a of respective first and second arms 212, 222 to enable relative pivotal movement between first and second arms 212, 222.

The needle 200 is positionable between a locked state (FIG. 3A) and an unlocked state (FIG. 3B) upon relative pivoting movement between first and second end portions 210, 220. In the locked state, mating or locking feature 214 of first end portion 210 is engaged with mating or locking feature 224 of second end portion 220 so that first end portion 210 and second end portion 220 are releasably locked together, at least temporarily, in an elongated arrangement. In the unlocked state, mating or locking feature 214 of first end portion 210 is disengaged from mating or locking feature 224 of second end portion 220 and one or both of first and second end portions 210, 220 are adapted to pivot about pin 230 relative to the other of first and second end portions 210, 220. As can be appreciated, one or both of first and second end portions 210, 220 is/are pivoted, away from the other of first and second end portions 210, 220, about pin 230, and toward the elongated arrangement to position needle 200 in the locked state. By comparison, one or both of first and second end portions 210, 220 is/are pivoted, toward the other of first and second end portions 210, 220, about pin 230, and away from the elongated arrangement.

Figure 4A:
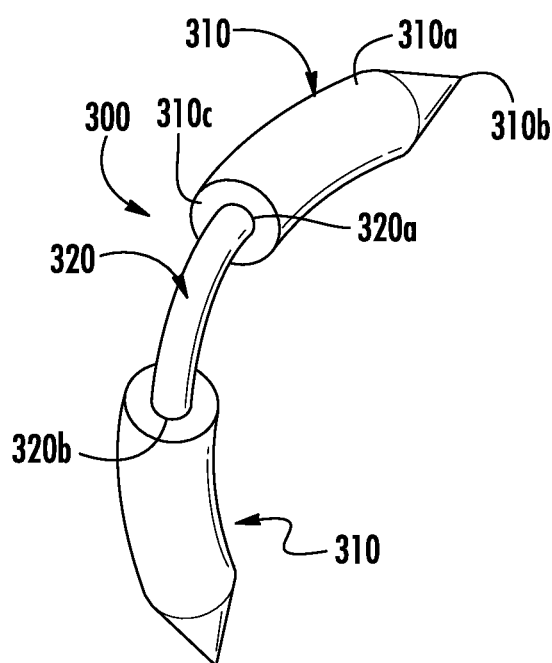
FIG. 4A is a perspective view of another embodiment of a needle shown in an unbent configuration.
Figure 4B:
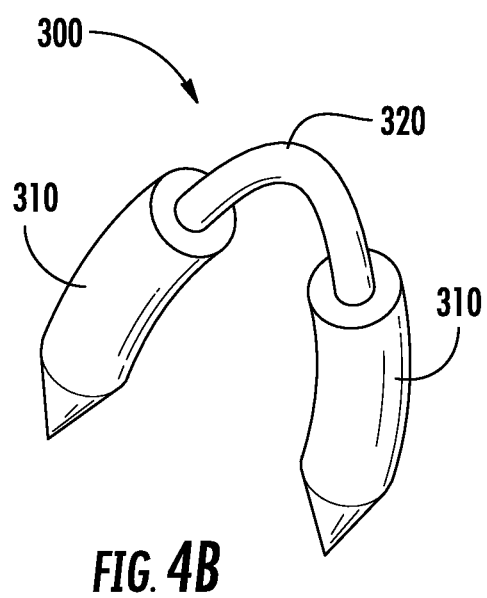
FIG. 4B is a perspective view of the needle of FIG. 4A shown in a bent configuration.

With reference to FIGS. 4A and 4B, another embodiment of a needle, shown generally as 300, is provided that can be used with an end effector of an endoscopic stitching device such as end effector 100. Needle 300 includes a pair of end portions 310 connected by a connection portion 320 having a pair of opposed ends 320a, 320b. Each end portion of the pair of end portions 310 includes a body 310a having a tip end 310b and a support end 310c. Each of the opposed ends 320a, 320b of connection portion 320 is secured to a support end 310c of one of the pair of end portions 310 to couple the pair of end portions 310 together. Connection portion 320 (and/or one or both of end portions 310, 320) is formed of a flexible material adapted to enable the pair of end portions 310 to pivot between an unbent configuration (FIG. 4A) and a bent configuration (FIG. 4B), including various intermediate configurations. In embodiments, connection portion 320 (and/or one or both of end portions 310, 320) can be formed of a shape memory material such as Nitinol or a suitable electroactive polymer. In some embodiments, connection portion 320 (and/or one or both of end portions 310, 320) can be adapted to move between the unbent and bent configurations in response to changes in temperature and/or induced stress/pressure.

Needles 200 and 300 can be utilized with any suitable end effector such as end effectors 40 and 100 to enable the respective end effector to support one of the respective needles 200, 300 while maintaining a minimal profile suitable for insertion and/or removal through small openings such as, for example, through a 10 millimeter diameter cannula (not shown).

In use, with reference again to FIG. 2A and with particular regard to operation of needle 200, jaw members 110, 120 of end effector 100 are closed for insertion so that needle 200, supported by end effector 100, is disposed in an insertion position or an unlocked state. More specifically, in the unlocked state, first and second end portions 210, 220 of needle 200 are at least partially approximated with first end portion 210 of needle 200 supported in needle receiving recess 112 of end effector 100 and second end portion 220 of needle 200 supported in needle receiving recess 122 of end effector 100.

With reference to FIGS. 2A-2C, jaw members 110, 120 of end effector 100 can be opened, for example, upon insertion into a surgical site, so that while first end portion 210 of needle 200 is maintained within needle receiving recess 112 of end effector 100, e.g., by engagement with grasping member 162, second end portion 220 of needle 200 is drawn from needle receiving recess 122 of end effector 100, e.g., while disengaged from grasping member 164. With first end portion 210 secured to jaw member 110, opening movement of one or both jaw members 110, 120 of end effector 100 enables second end portion 220 of needle 200 to pivot about pivot pin 230 relative to first end portion 210 of needle 200 as second end portion 220 cams out of second needle receiving recess 122. As jaw members 110, 120 move from the insertion state (FIG. 2A) to the stitching state (FIG. 2B), needle receiving recess 122 cams second end portion 220 relative to first end portion 210 until needle 200 is elongated and positioned in the locked state (see FIG. 2B).

Alternatively, and or additionally, guide member 140 can be advanced distally and/or proximally, for example, upon an actuation of actuation mechanism 150, to engage second end portion 220 of needle 200 (e.g., with a distal end portion of guide member 140) and provide axial force to second end portion 220 to facilitate movement of second end portion 220 and orient needle 200 into the locked state. As can be appreciated, guide member 140 can be adapted to be translated distally and/or proximally as necessary to facilitate a positioning of needle 200 into the locked state. Additionally or alternatively, needle 200, in some embodiments, can be oriented from the unlocked state to the locked state while simultaneously secured to both jaw members 110, 120 (e.g., with first and second end portions at least partially secured within respective needle receiving recesses 112, 122 of jaw members 110, 122 by partially advanced grasping members 162, 164).

Upon positioning needle 200 in the locked state, end effector 100 can then be used to effectuate a suturing procedure similar to that described in U.S. Pat. No. 8,337, 515 referenced above. For example, handle assembly 20 is actuated to pivot one or both of first and second jaw members 110, 120 between open and closed states for passing needle 200 between jaw members 110, 120 and drawing suture "S" through tissue. More particularly, with needle 200 secured to needle receiving recess 112 of first jaw member 110 (e.g., with grasping member 162), an actuation of a trigger 24 (FIG. 1) other actuator of handle assembly 20 closes jaw members 110, 120 around tissue so that needle 200 pierces the tissue and is guided into needle receiving recess 122 of the second jaw member 120 to secure needle 140 thereto (e.g., with grasping member 164) and effectuate a first stitch. As can be appreciated, grasping member 164 can be distally advanced while grasping member 162 is proximally withdrawn to effectuate the transference of needle 200 between jaw members 110, 120. In embodiments, each grasping member 162, 164 can be distally advanced and/or proximally withdrawn independent of the other grasping member 162, 164. In some embodiments, grasping members 162, 164 can be simultaneously proximally withdrawn and/or simultaneously distally advanced.

After completion of the first stitch, jaw members 110, 120 can then be opened again so that needle 200 can be transferred back from second jaw member 120 to the first jaw member 110 in like fashion upon another closing of jaw members 112, 114 to effectuate another stitch. This process, in whole, or in part, can be repeated as necessary until the tissue is sutured as desired.

Upon completion of the suturing procedure, guide member 140 can be positioned to receive second end portion 220 of needle 200 within opening 142 of guide member 140 to facilitate a pivoting movement of second end portion 220 of needle 200 relative to first end portion 210 of needle 200 when needle 200 is retained in needle receiving recess 112 (e.g., friction fit and/or grasping member 162). For example, when needle 200 is disposed in a locked state, second end portion 220 of needle 200 can be positioned within opening 142 of guide member 140, such as by translating guide member 140 and/or pivoting jaw members 110, 120 of end effector 100 as appropriate. Then, a subsequent sufficient proximal movement of guide member 140 can impart an axial and/or rotational force on second end portion 220 of needle 200 to unlock first and second end portions 210, 220 of needle 200. Upon unlocking needle 200, jaw members 110, 120 of end effector 100 and/or guide member 140 can be manipulated as appropriate to reposition first and second end portions 210, 220 within respective needle receiving recesses 112, 122 of respective first and second jaw members 110, 120 so that end effector 100 can be closed around needle 200 and back into the insertion position, for example, for removal from the surgical site.

Since the operation of needle 300 is similar to the use of needle 200 as detailed above, the operation of needle 300 is only described herein to the extent necessary to describe the differences in operation of needle 300. Needle 300 can be positioned in the bent or approximated configuration (FIG. 4B), for example, while supported by an end effector such as end effector 100 or 100, to enable the end effector to maintain a minimal profile during insertion and/or removal to/from a surgical site (e.g., through a small surgical or natural opening). Needle 300 can also be arranged in the unbent or unapproximated configuration (FIG. 4A), for example, to effectuate surgical suturing when coupled to the end effector upon being advanced to a surgical site. Due to the flexibility of connecting portion 320 of needle 300, needle 300 can be positioned between the bent and unbent configurations by a predetermined pivoting movement of jaw members of any suitable end effector and/or by predetermined actuation of any guide feature, such as guide member 140 of end effector 100. More particularly, needle 300 can be manipulated as necessary to achieve the minimal profile arrangement between needle 300 and the respective end effector supporting needle 300. However, connecting portion 320 has sufficient rigidity to enable needle 300 to be utilized to perform a suturing procedure.

In temperature responsive embodiments of needle 300, for example, needle 300 is biased or urged from the bent configuration to the unbent configuration upon being subject to a predetermined temperature such as body temperature. Once inserted in the body, the temperature responsive properties of this embodiment of needle 300 maintain the needle 300 in the unbent configuration so that needle 300 can be used to effectuate a suturing procedure.

When finished suturing with the temperature responsive embodiment of needle 300, removal from the surgical site may be achieved by releasing needle 300 from both jaw members of one of the presently described end effectors and separating needle 300 from the end effector (e.g., with a separate grasping device) so that the end effector may be closed and withdrawn through the access device separate from needle 300.

As another example, in stress/pressure responsive embodiments of needle 300, needle 300 is biased or urged from the bent configuration to the unbent configuration upon being subject to a predetermined stress or pressure such as compressive closure force(s) imparted through an end effector that is greater than the closure force(s) required to effectuate a suturing procedure. More particularly, this embodiment of needle 300 has sufficient rigidity to effectuate a suturing procedure; however, this embodiment of needle 300 will bend upon an application of a predetermined amount of compressive closure force(s) that is greater than a rigidity threshold of the needle that is suitable for suturing. Thus, to remove from the surgical site when finished suturing, compressive closure forces can be applied to this embodiment of needle 300 that are greater than the closure forces required for suturing to thereby bend this embodiment of needle 300 back into the bent configuration to enable the end effector to achieve the minimal profile required during insertion. This minimal profile will enable a simultaneous removal of this embodiment 300 and the end effector. Alternatively, and/or additionally, this embodiment of needle 300 can be released from the end effector so that each is separately withdrawn as described above.

Figure 5:
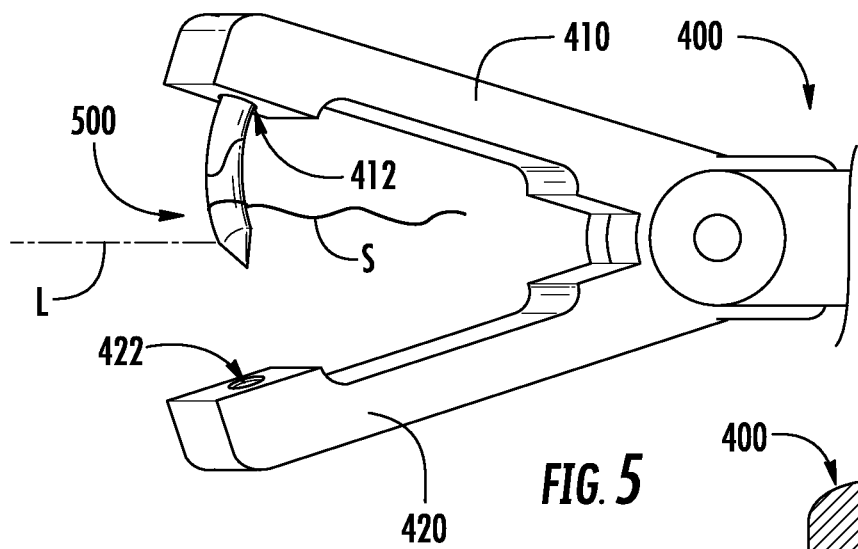
FIG. 5 is a side, perspective view of a distal end portion of another embodiment of an end effector of the endoscopic stitching device of FIG. 1 in an open state, this embodiment of the end effector shown supporting another embodiment of a needle in accordance with the present disclosure.

FIG. 5 illustrates another embodiment of an end effector, shown generally as 400, supporting another embodiment of a needle, shown generally as 500 and described in greater detail below. End effector 400 is substantially similar to end effector 100 and is only described herein to the extent necessary to describe the differences in operation and construction. End effector 400 is adapted for use with an endoscopic stitching device and includes a first jaw member 410 and a second jaw member 420 that are pivotally connected. First jaw member 410 defines a first needle receiving recess 412 and second jaw member 420 defines a second needle receiving recess 422. First and second jaw members 410, 420 are adapted for relative movement between open and closed states for effectuating a suturing procedure, for example, by passing needle 500, with suture "S" coupled to needle 500, back and forth through tissue between first and needle receiving recesses 412, 422 of respective first and second jaw members 410, 420 similar to that described above with respect to end effector 100 and needle 200.

Figure 6A:
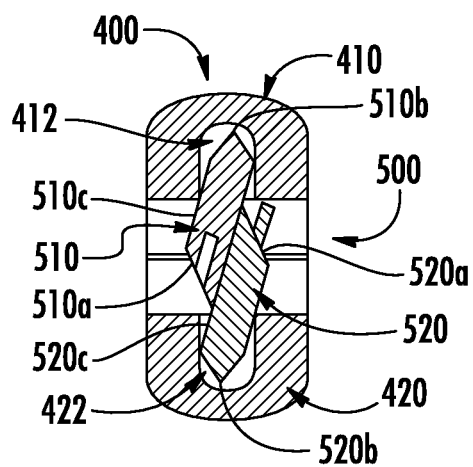
FIGS. 6A-6C are progressive, front, cross-sectional views illustrating the end effector of FIG. 5 coupling first and second end portions of the needle of FIG. 5.
Figure 6B:
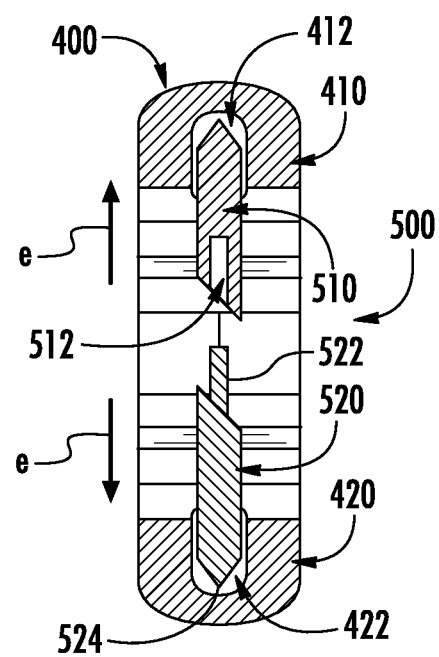
Figure 6C:
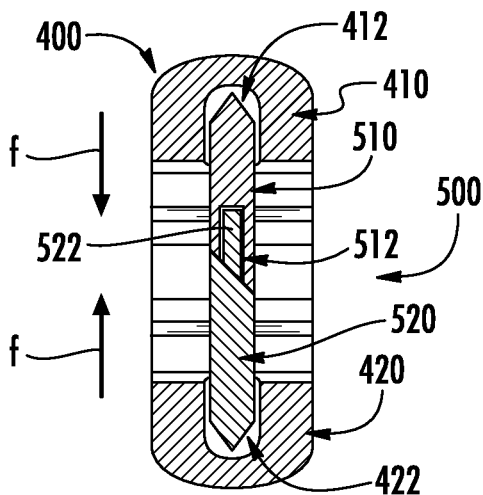

As seen in FIGS. 6A-6C, needle 500 includes a first end portion 510 and a second end portion 520. First end portion 510 includes a connecting end 510a, an opposed tip end 510b, and an outer surface 510c. A mating recess 512 is defined in connecting end 510a. Mating recess 512 may be formed in any suitable shape (e.g., circular and non-circular cross-sections including any polygonal shape). Tip end 510b is adapted to be releasably received within needle receiving recess 412 of end effector 400. Second end portion 520 includes a connecting end 520a, an opposed tip end 520b, and an outer surface 520c. A mating protuberance 522 (e.g., bump, nub, rod, etc.) is located on connecting end 520a of second end portion 520. Mating protuberance 522 is complementary to (e.g., keyed to) mating recess 512 of first end portion 510. In embodiments, first end portion 510 includes a mating protuberance and second end portion 520 defines a mating recess.

In an insertion position, as seen in FIG. 6A, first and second end portions 510, 520 of needle 500 are supported by end effector 400 in a first, laterally misaligned configuration. End effector 400 can include a pair of grasping members (not shown) similar to grasping members 162, 164 described above. Each grasping member of the pair of grasping members is adapted to engage one of first and second end portions 510, 520 such that the pair of grasping members simultaneously support both first and second end portions 510, 520 during insertion into a surgical site.

In the laterally misaligned configuration, tip ends 510b, 520b of respective first and second end portions 510, 520 of needle 500 are secured within respective needle receiving recesses 412, 422 of end effector 400 and disposed in longitudinally aligned relation to one another, while connecting ends 510a, 520a (and respective mating recess and protuberance 512, 522) of respective first and second end portions 510, 520 of needle 500 are separated and disposed in laterally-adjacent relation with one another with each end portion 510, 520 imposing a lateral force on the other to maintain first and second end portions 510, 520 in the misaligned configuration. Further, in the misaligned configuration, connecting end 510a of first end portion 510 can be closer to second jaw member 420 than first jaw member 410 and connecting end 520a of second end portion 520 can be closer to first jaw member 410 than second jaw member 420. In addition, connecting ends 510a, 520a of respective first and second end portions 510, 520 can be spaced apart such that outer surfaces 510c, 520c of respective first and second end portions 510, 520 are disposed in contacting relation when first and second end portions 510, 520 are misaligned. Although first end portion 510 is shown left (when viewed from the front of device) of second end portion 520 in the insertion position, second end portion 520 can be positioned left of first end portion 510 in the insertion position.

With reference to FIG. 6B, first and second jaw members 410, 420 can be unapproximated (as indicated by arrows "e"), for example, subsequent to an insertion, so that first and second end portions 510, 520 are drawn apart until disposed in spaced-apart relation. By virtue of being spaced-apart, first and second end portions 510, 520 no longer impose lateral forces on one another, enabling first and second end portions 510, 520 to rotate about the respective first and second jaw members 410, 420 in opposite radial directions until aligned with one another relative to the longitudinal axis. When first and second end portions 510, 520 are aligned relative to the longitudinal axis, mating recess 512 and mating protuberance 522 of respective first and second end portions 510 are longitudinally aligned.

As seen in FIG. 6C, first and second jaw members 410, 420 can then be approximated (as indicated by arrows "f"), connecting first and second end portions 510, 520 via respective mating recess and protuberance 512, 522. The connection of first and second end portions 510, 520 forms needle 500 into a unitary arrangement suitable for use in a suturing procedure. To effectuate the suturing procedure and pass needle 500 back and forth between first and second jaw members 410, 420, the grasping members are movable in alternate distal and/or proximal relation relative to one another and first and second jaw members 410, 420 are moveable between open and closed states.

Upon completion of the suturing procedure, needle 500 can be released from end effector 400 so that each is separately withdrawn as described above with respect to the temperature responsive embodiment of needle 300.

Figure 7:
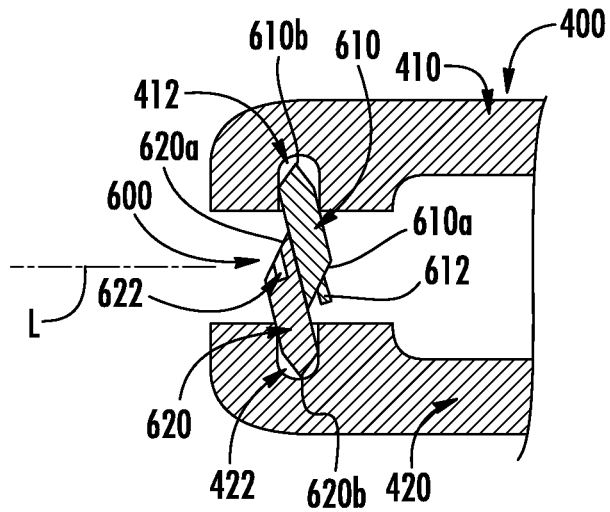
FIG. 7 is a side, cross-sectional view of the embodiment of the end effector of FIG. 5 supporting another embodiment of a needle in accordance with the present disclosure.

Rather than having end portion 510, 520 oriented in offset lateral relation, the end portions of the needle may be oriented in longitudinal offset relation as shown in the embodiment of FIG. 7. FIG. 7 illustrates another embodiment of a needle, shown generally as needle 600 positioned in end effector 400 in an insertion position. Needle 600 is substantially similar needle 500 and is only described herein to the extent necessary to describe the differences in construction and operation of needle 600. Needle 600 includes a first end portion 610 and a second end portion 620. First end portion 610 has a connecting end 610a and a tip end 610b. Connecting end 610a includes a mating protuberance 612. Second end portion 620 has connecting end 620a and a tip end 620b. Connecting end 620a of second end portion 620 includes a mating recess 622 that is complementary to mating protuberance 612 of first end portion 610. In the insertion position, connecting ends 610a, 620a (and respective mating protuberance and recess 612, 622) of respective first and second end portions 610, 620 are disposed in longitudinally adjacent relation to one another, while tip ends 610b, 620b are disposed in longitudinally aligned relation to one another. Although first end portion 610 is shown proximally of second end portion 620 in this insertion position, second end portion 620 can be positioned proximally of first end portion 610 in this insertion position.

In use, similar to that described above with respect to needle 500, end effector 400 can be moved between an open or unapproximated position and a closed or approximated position to couple first and second end portions 610, 620 into a unitary arrangement that forms needle 600. Needle 600 can then be utilized to effectuate a suturing procedure as described above with respect to needle 500 and end effector 400. Upon completion of the suturing procedure, needle 600 and/or end effector 400 can be removed from the surgical site as described above with respect to needle 500 and end effector 400.

As can be appreciated, although the embodiments of first and second end portions of needles 500 and 600 are shown positioned in offset lateral (FIG. 6A) and/or longitudinal (FIG. 7) relation in the respective insertion positions of needles 500, 600, any of the first and second end portions, or portions thereof, of the needles 500, 600 can be disposed in any suitable relation to any opposed first and/or second end portion, or portions thereof, of the needles 500, 600, including laterally, longitudinally, and/or combinations thereof.

Figure 8A:
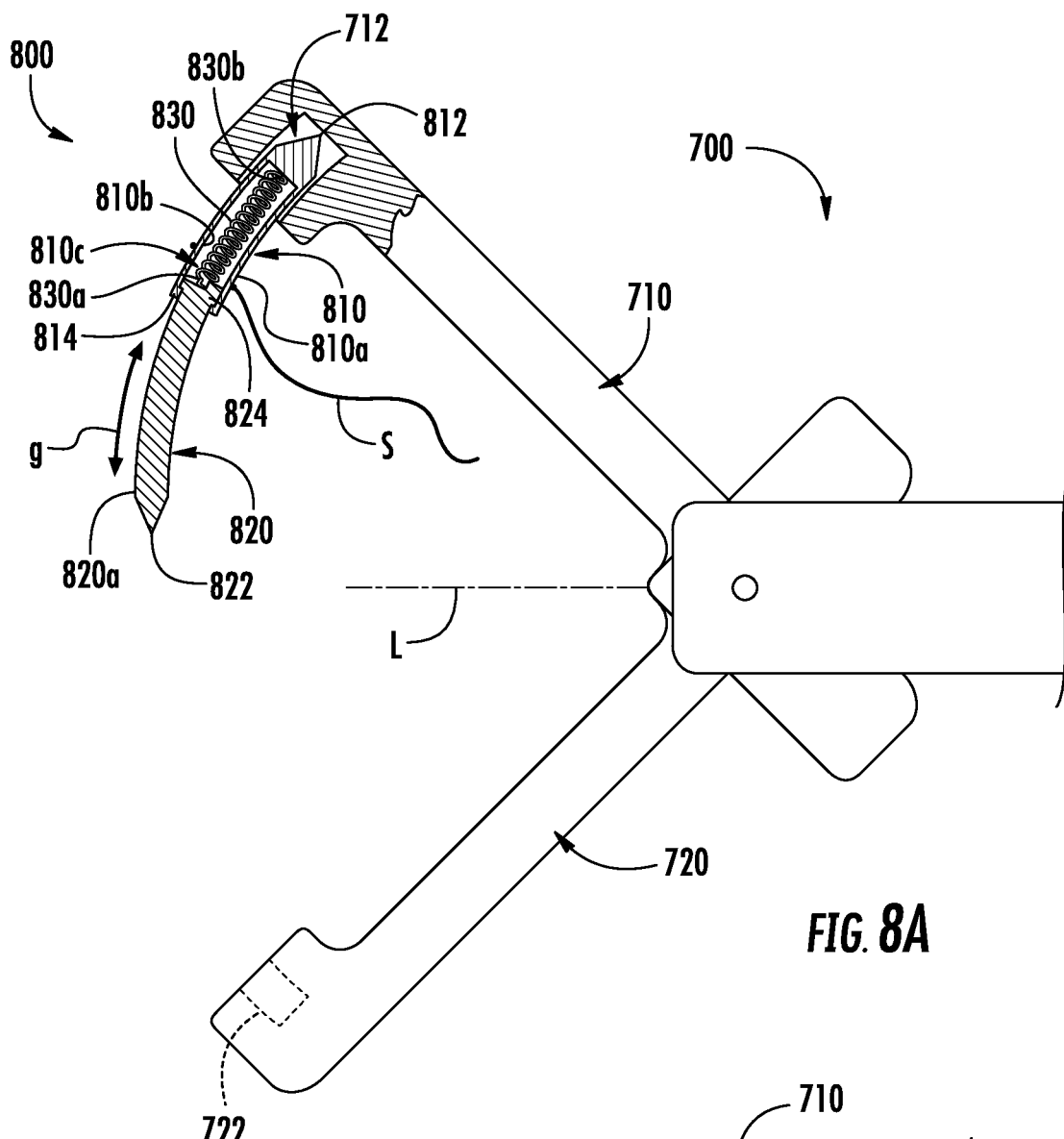
FIG. 8A is a side view, in partial cross-section, of another embodiment of an end effector of the endoscopic stitching device of FIG. 1 in an open state supporting another embodiment of a needle in accordance with the present disclosure, the needle being shown in an extended position.
Figure 8B:
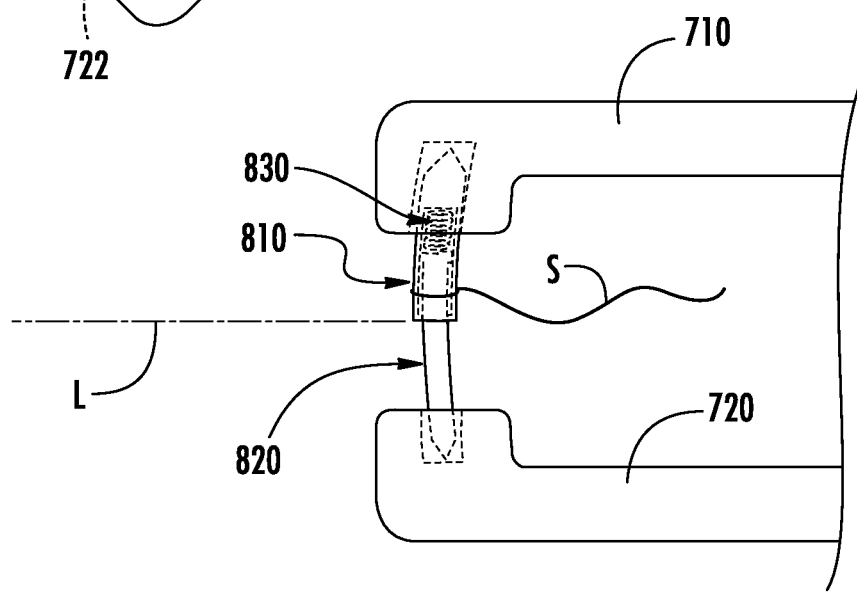
FIG. 8B is a side view, in partial cross-section, of a distal end portion the end effector shown in FIG. 8A in a closed state supporting the needle of FIG. 8A, the needle being shown in a compressed position.

FIGS. 8A and 8B illustrate another embodiment of an end effector, shown generally as 700, that supports another embodiment of a needle, shown generally as 800. End effector 700 is substantially similar to end effectors 40 and 400 and is only described herein to the extent necessary to describe the differences in operation and construction of end effector 700. End effector 700 is adapted for use with an endoscopic stitching device and includes a first jaw member 710 and a second jaw member 720 that are pivotally connected. First jaw member 710 defines a first needle receiving recess 712 and second jaw member 720 defines a second needle receiving recess 722. First and second jaw members 710, 720 are adapted for relative movement between open and closed states for effectuating a suturing procedure.

As seen in FIG. 8A, needle 800 is adapted to support a suture "S" and includes a first end portion 810, a second end portion 820, and a compressible element 830 supported between first and second end portions 810, 820 to enable second end portion 820 to slidably translate through first end portion 810 (as indicated by arrow "g"), relative to first end portion 810, between a first, compressed position and a second, extended position. The compressible element 830 can be adapted to bias first and second end portions 810, 820 towards the extend position. First end portion 810 has an outer surface 810a and an inner surface 810b. Inner surface 810b defines a cavity 810c. Cavity 810c is dimensioned to support compressible element 830. First end portion 810 includes a tip end 812 and a support end 814. Second end portion 820 has an outer surface 820a and includes a tip end 822 and a support end 824. Compressible member 830 is formed of a compressible material and includes a first end 830a and a second end 830b. First end 830a is secured to a trailing end of support end 824 of second end portion 820 in a leading end portion of cavity 810c. Second end 830b is secured to a trailing end portion of cavity 810c adjacent to tip end 812 of first end portion 810. Compressible member 830 can include a spring. In embodiments, compressible member 830 includes gas.

An approximation of first and second jaw members 710, 720 of end effector 700 compresses needle 800 from an extended position (FIG. 8A) to a retracted or compressed position (FIG. 8B). In the compressed position, needle 800 enables end effector 700 to maintain a minimal profile for insertion and/or removal of end effector 700 and needle 800 through a small opening. In the extended position, needle 800 can be used to effectuate a suturing procedure.

Any of the components of the presently described devices can be formed of any suitable metallic and/or polymeric material. Securement of any of the components of the presently described devices to any of the other components of the presently described devices can be effectuated using known fastening techniques such welding (e.g., ultrasonic), crimping, gluing, etc.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. For example, when finished using the present minimally invasive suturing devices, removal from the surgical site may be achieved while one of the presently described needles is secured to one of the presently described end effectors by sequentially pulling the access device and the end effector out of the incision in the patient's skin, with the access device being removed first (while remaining supported about the shaft of the suturing device) and the end effector being removed second. More particularly, with the access device removed, the end effector can be readily drawn through the incision since the patient's skin will have sufficient elasticity to enable removal of the end effector without reducing the height of the end effector. Subsequent to the removal of the end effector through the incision, the access device can be removed from the suturing device by advancing the access device off of the distal end of the end effector.

Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An endoscopic stitching device, comprising:
an end effector including a first jaw member and a second jaw member, the first jaw member movable relative to the second jaw member between an open state and a closed state; and
a needle removably coupled to the end effector and configured to alternate between the first jaw member and the second jaw member of the end effector, the needle including:
  a first end portion and a second end portion, each of the first and second end portions of the needle releasably engageable with a respective one of the first and second jaw members of the end effector; and
  a connecting portion disposed between the first and second end portions, the connecting portion configured to enable the first end portion to move relative to the second end portion between approximated and unapproximated positions as the first and second jaw members move between the open and closed states, wherein the connecting portion of the needle includes a first arm member that extends from the first end portion of the needle and a second arm member that extends from the second end portion of the needle, the first arm member secured to the second arm member by a pivot pin, the first end portion configured to pivot about the pivot pin relative to the second end portion.

2. The endoscopic stitching device of claim 1, wherein the first arm member of the needle includes a protuberance and the second arm member of the needle includes a recess, the protuberance and the recess configured to selectively engage each other to at least temporarily lock the first and second end portions of the needle in an aligned configuration.

3. The endoscopic stitching device of claim 1, wherein the needle includes at least one of a metallic or polymeric material.

4. An endoscopic stitching device, comprising:
a first jaw member;
a second jaw member, the first and second jaw members positioned to move between open and closed states; and
an endoscopic stitching needle configured to alternate between the first jaw member and the second jaw member, the needle comprising:
  a first end portion configured to releasably engage the first jaw member; and
  a second end portion configured to releasably engage the second jaw member;
  a connecting portion joining the first and second end portions, the connecting portion configured to enable the first end portion to move relative to the second end portion between approximated and unapproximated positions as the first and second jaw members move between open and closed states, wherein the connection portion includes a first arm member and a second arm member, the first and second arm members configured to selectively engage one another to selectively lock the first and second end portions in a first configuration.

5. The endoscopic stitching device of claim 4, wherein the first arm member extends from the first end portion and the second arm member extends from the second end portion, the first arm member secured to the second arm member by a pivot pin, the first end portion configured to pivot about the pivot pin relative to the second end portion.

6. The endoscopic stitching device of claim 5, wherein the first arm member includes a protuberance and the second arm member includes a recess, the protuberance and the recess configured to selectively engage each other to move the first and second arm members between locked and unlocked positions.

7. The endoscopic stitching device of claim 6, wherein the first and second arm members are in the locked position when the protuberance is engaged with the recess, and the first and second arm members are in the unlocked position when the protuberance is disengaged from the recess.

8. The endoscopic stitching device of claim 4, wherein the needle includes at least one of a metallic or a polymeric material.

9. The endoscopic stitching device of claim 4, wherein the first arm member includes a protuberance and the second arm member includes a recess, the protuberance and the recess configured to selectively engage one another.

10. The endoscopic stitching device of claim 9, wherein the first and second end portions are selectively locked together when the protuberance is received within the recess.

11. The endoscopic stitching device of claim 10, wherein the first and second end portions are aligned with one another when locked together.

12. The endoscopic stitching device of claim 4, wherein the first configuration is an aligned configuration.

13. The endoscopic stitching device of claim 4, wherein the first and second arm members are pivotably coupled together.

* * * * *